United States Patent
Larsen et al.

(10) Patent No.: US 11,259,130 B2
(45) Date of Patent: Feb. 22, 2022

(54) HEARING ASSISTIVE SYSTEM WITH SENSORS

(71) Applicant: Widex A/S, Lynge (DK)

(72) Inventors: Soren Mollskov Larsen, Varlose (DK); Morten Kroman, Taastrup (DK)

(73) Assignee: Widex A/S, Lynge (DK)

( * ) Notice: Subject to any disclaimer, the term of this patent is extended or adjusted under 35 U.S.C. 154(b) by 20 days.

(21) Appl. No.: 16/712,141

(22) Filed: Dec. 12, 2019

(65) Prior Publication Data

US 2020/0196071 A1    Jun. 18, 2020

Related U.S. Application Data

(60) Provisional application No. 62/779,580, filed on Dec. 14, 2018.

(51) Int. Cl.
  *H04R 25/00* (2006.01)
  *A61B 5/00* (2006.01)
  *A61B 5/291* (2021.01)

(52) U.S. Cl.
  CPC .......... *H04R 25/554* (2013.01); *A61B 5/291* (2021.01); *A61B 5/6817* (2013.01);
  (Continued)

(58) Field of Classification Search
  CPC ..... A61B 5/291; A61B 5/6817; A61B 2/0219; H04R 25/554; H04R 25/505; H04R 25/552; H04R 2460/00; H04R 1/028
  See application file for complete search history.

(56) References Cited

U.S. PATENT DOCUMENTS 9,210,517 B2 * 12/2015 Pontoppidan ........ H04R 25/305
9,742,471 B1 *  8/2017 Thoen ...................... H04W 4/80
(Continued)

FOREIGN PATENT DOCUMENTS

DE   10 2015 015 113 A1    5/2017
EP       2 967 366 A1      1/2016
(Continued)

OTHER PUBLICATIONS

Chi-Chun Chen et al. "A Tail-Worn Sensor-Equipped Heart Rate Measurement Apparatus for Ischemic Stroke Prevention ", Department of Electronic Engineering, National Chin-Yi University of Technology, Taichung, Taiwan; Research Article—Neuropsychiatry, 2018, vol. 8, Issue 1.

(Continued)

*Primary Examiner* — Brian Ensey
(74) *Attorney, Agent, or Firm* — Sughrue Mion, PLLC

(57) ABSTRACT

A hearing assistive system including a first hearing assistive device adapted for wireless communication with second hearing assistive device, wherein the first hearing assistive device and the second hearing assistive device have at least one sensor adapted for acquiring a physiological signal each. The first hearing assistive device is adapted for providing a synchronization signal to the second hearing assistive device and instructing the second hearing assistive device to acquire the physiological signal based on timing instructions. The second hearing assistive device is adapted for acquiring the physiological signal by means of the sensor according to the received timing instructions and transmitting the acquired physiological signal wirelessly to the first hearing assistive device. The first hearing assistive device includes a processor for processing the synchronized, physiological signals acquired by sensors of the first hearing (Continued)

assistive device and the second hearing assistive device and synchronized via wireless communication.

20 Claims, 3 Drawing Sheets

(52) U.S. Cl.
CPC .... *H04R 25/505* (2013.01); *A61B 2562/0219* (2013.01); *H04R 25/552* (2013.01)

(56) References Cited

U.S. PATENT DOCUMENTS

| | | |
|---|---|---|
| 2005/0249368 A1 | 11/2005 | Menzl et al. |
| 2013/0172691 A1 | 7/2013 | Tran |
| 2013/0343584 A1* | 12/2013 | Bennett ............ H04R 25/554 381/315 |
| 2014/0257058 A1 | 9/2014 | Clarysse et al. |
| 2014/0321682 A1 | 10/2014 | Kofod-Hansen et al. |
| 2015/0157220 A1 | 6/2015 | Fish et al. |
| 2015/0157262 A1 | 6/2015 | Schuessler et al. |
| 2017/0042425 A1 | 2/2017 | Ramlall et al. |
| 2018/0092554 A1 | 4/2018 | Zhang et al. |

FOREIGN PATENT DOCUMENTS

| | | |
|---|---|---|
| EP | 2 997 893 A1 | 3/2016 |
| EP | 3 035 710 A2 | 6/2016 |
| EP | 3 185 590 A1 | 6/2017 |
| EP | 3 291 730 A1 | 3/2018 |
| WO | 2012/063172 A1 | 5/2012 |
| WO | 2015/024585 A1 | 2/2015 |
| WO | 2016/065476 A1 | 5/2016 |

OTHER PUBLICATIONS

Matej Marinko, "Continuous Blood Pressure Estimation from PPG Signal", Faculty of Mathematics and Physics, Jadranska cesta 19, 1000 Ljubljana; Informatica 42, 2018, vol. 33-42.

Hao Lin et al., "Noninvasive and Continuous Blood Pressure Monitoring Using Wearable Body Sensor Networks", Northeastern University, China; IEEE Intelligent Systems, Nov.-Dec. 2015, vol. 30, Issue: 6.

Communication dated Mar. 4, 2020 from European Patent Office in EP Application No. 19211108.6.

* cited by examiner

HEARING ASSISTIVE SYSTEM WITH SENSORS

CROSS-REFERENCE TO RELATED APPLICATIONS

This application claims benefit of provisional application No. 62/779,580 filed Dec. 14, 2018, the disclosure of which is incorporated by reference herein.

The present invention relates to a hearing assistive system comprising two hearing assistive device adapted for wireless communication with each other and each having at least one sensor adapted for acquiring a physiological signal.

BACKGROUND OF THE INVENTION

Mobile devices, like a watch with sensors, are known as a fitness tracker. This is a device or application for monitoring and tracking fitness-related metrics such as distance walked or run, calorie consumption, and in some cases heartbeat and quality of sleep. The data is often loaded wirelessly into a computer or a smartphone for long-term data tracking.

The purpose of the invention is to provide a hearing assistive system acquiring synchronized physiologic signals processed form extracting characteristics of the sensor signals.

SUMMARY OF THE INVENTION

The invention is directed to a hearing assistive system comprising a first hearing assistive device adapted for wireless communication with second hearing assistive device; wherein the first hearing assistive device and the second hearing assistive device each have at least one sensor adapted for acquiring a physiological signal; wherein the first hearing assistive device is adapted for providing a synchronization signal to the second hearing assistive device, and instructing the second hearing assistive device to acquire the physiological signal based on timing instructions, wherein the second hearing assistive device is adapted for acquiring the physiological signal by means of the sensor according to the received timing instructions, and transmitting the acquired physiological signal wirelessly to the first hearing assistive device, wherein the first hearing assistive device comprises a processor for processing the synchronized, physiological signals acquired by sensors of the first hearing assistive device and the second hearing assistive device and synchronized via wireless communication.

The invention is further directed to a method of operating a hearing assistive system comprising a first hearing assistive device adapted for wireless communication with second hearing assistive device, the first hearing assistive device and the second hearing assistive device each have at least one sensor adapted for acquiring a physiological signal; wherein the method comprises steps of: providing, in the first hearing assistive device, a synchronization signal for the second hearing assistive device, instructing the second hearing assistive device to acquire the physiological signal based on timing instructions for synchronization, acquiring, in the second hearing assistive device, the physiological signal by means of the sensor according to the received timing instructions, transmitting the acquired physiological signal wirelessly to the first hearing assistive device, acquiring, in the first hearing assistive device, a physiological signal by means of the sensor according to the transmitted timing instructions, and processing in the first hearing assistive device the synchronized, physiological signals acquired by the sensors in the first hearing assistive device and the second hearing assistive device.

Preferred embodiments are described below and further defined in the dependent claims.

By extracting characteristics from the processed sensor signals, the extracted characteristics may be used for controlling an audio signal path with hearing loss alleviation in the individual hearing assistive device.

BRIEF DESCRIPTION OF THE DRAWINGS

The invention will be described in further detail with reference to preferred aspects and the accompanying drawing, in which.

DETAILED DESCRIPTION

Figure 1:
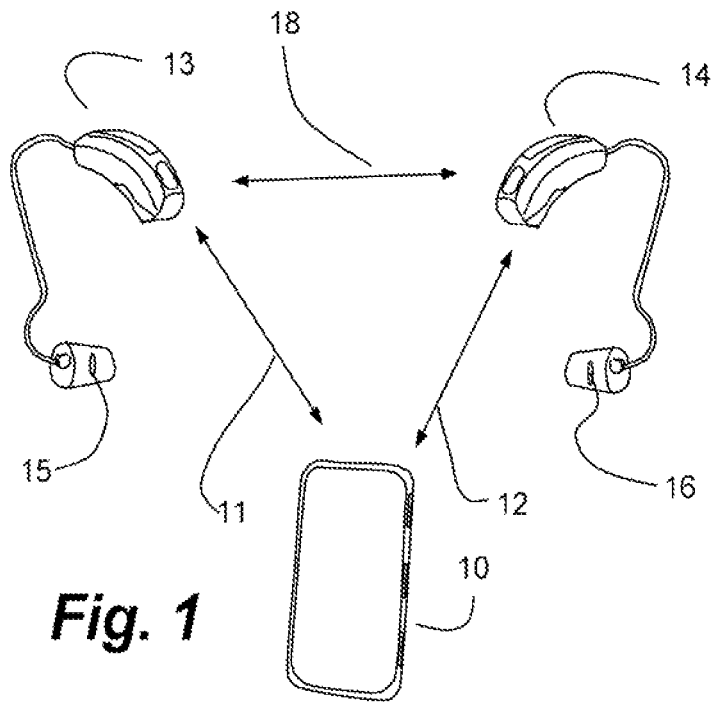
FIG. 1 illustrates one embodiment of a set of binaural hearing devices with sensors according to the invention.

FIG. 1 illustrates one embodiment of a set of binaural hearing devices with sensors according to the invention. In one embodiment, two hearing assistive devices 13 and 14, e.g. hearing aids each comprise a sensor 15 and 16, respectively, adapted for acquiring a physiological signal. The two hearing assistive devices 13 and 14 may communicate with a personal communication device 10 via wireless links 11 and 12. In one embodiment, the wireless links 11 and 12 may operate according to the Bluetooth Low Energy protocol.

Furthermore, the two hearing assistive devices 13 and 14 have a wireless link 18 for inter-ear communication. The wireless link 18 may in one embodiment be compatible with the wireless links 11 and 12 and may in another embodiment operate according to a proprietary protocol based on e.g. Frequency Modulation with a carrier frequency in the range of 5-20 MHz, whereby energy loss due to organic tissue will be minimized.

The sensors 15, 16 are in one embodiment PPG (photoplethysmogram) sensors. The PPG sensors 15, 16 obtains optically a plethysmogram which is a volumetric measurement of an organ. A PPG sensor is often used for obtaining a photoplethysmogram by using a pulse oximeter illuminating the skin and measures changes in light absorption. Such a pulse oximeter monitors the perfusion of blood to the dermis and subcutaneous tissue of the skin.

In one embodiment, the sensors 15, 16 are electrodes provided on ear molds for sensing an EEG signal from the ear canal of the hearing assistive device user.

In some embodiments, two hearing assistive devices 13 and 14 each include at least one accelerometer integrated in the Behind-The-Ear housing. The accelerometer may be a multi-axis accelerometer adapted for detecting magnitude and direction of the acceleration, as a vector quantity. The accelerometer can be used to sense orientation, coordinate acceleration, vibration, shock, and falling. The accelerometer may be a microelectromechanical systems (MEMS) accelerometer.

The requesting hearing assistive device 13 is adapted for providing a synchronization signal for acquiring synchronized sensor signal from the two hearing assistive devices 13, 14, and for instructing the sensing hearing assistive device for triggering the acquisition of the physiological signal. The sensing hearing assistive devices 14 is adapted for acquiring the physiological signal according to the received timing instructions and for transmitting the acquired, synchronized physiological signal wirelessly to the requesting hearing assistive device 13. The requesting hearing assistive device 13 comprises a processor for processing the synchronized physiological signal acquired by the at least two sensors in the requesting hearing assistive device 13 and the sensing hearing assistive devices 14, respectively.

According to one embodiment of the invention, the wireless, synchronized sensors 15, 16 are configured as multi-site sensor network. Hereby, simultaneous measurements from e.g. the right and left ear lobes and/or other appropriate body parts may be carried out wirelessly. Multi-site sensors offer significant potential for data mining, e.g. via deep learning, as well as a range of innovative pulse wave analysis techniques.

In one embodiment the two hearing assistive devices 13 and 14 are alternately operating as requesting hearing assistive device and sensing hearing assistive device. Hereby the two hearing assistive devices 13 and 14 are both processing sensor signals from its own sensor and the counterpart's sensor.

In one embodiment, one of the two hearing assistive devices act as requesting hearing assistive device 13 but share own sensor signal with the sensing hearing assistive device 14. The sharing includes also timing details enabling the sensing hearing assistive device 14 to process its own sensor signals and shared sensor signals in synchronized processing.

In one embodiment, one of the two hearing assistive devices acts as requesting hearing assistive device 13 processing sensor signals from its own sensor and the counterpart's sensor. The requesting hearing assistive device 13 then just shares the extracted characteristics found by processing own sensor signals and shared sensor signals in synchronized processing to the sensing hearing assistive device 14.

Figure 2:
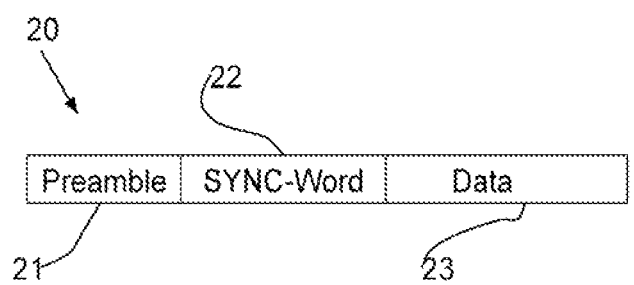
FIG. 2 illustrates the structure of a synchronization message sent from a requesting hearing assistive device to a sensing hearing assistive device according to one embodiment of the invention.
Figure 3:
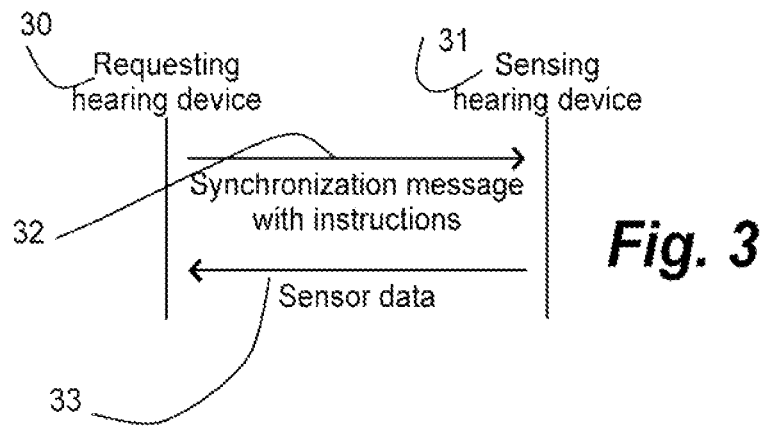
FIG. 3 illustrates the messaging structure between a requesting hearing assistive device and a sensing hearing assistive device according to one embodiment of the invention.

FIGS. 2 and 3 illustrate that a synchronization message 32 has a payload 20 including a preamble 21, a sync-word 22 and data bits 23. The synchronization message 32 is sent from a requesting hearing assistive device 30 to a sensing hearing assistive device 31 according to one embodiment of the invention. The sensing hearing assistive device 31 can detect the frequency of the signal and adjust its own clock frequency to the received signal by means of the preamble 21. The purpose of the clock frequency adjustment is essentially to find the center of the data bits. Furthermore, the preamble 21 is used to facilitate DC Compensation. In one embodiment, the preamble 21 is a fixed zero-one pattern of four symbols. The preamble is followed by the sync-word 22 which is used for determining the time of arrival of the first data bit and for estimating the time of later messages. In one embodiment, the sync-word 22 is a 64-bit code word preferably derived from the addresses of the devices involved in the communication. In one embodiment, the sync-word 22 is constructed to ensure a large Hamming distance between sync-words 22 used in different communications supervised by the requesting hearing assistive device 30. This provides good auto correlation properties of the sync-word 22 which improves timing acquisition. According to one embodiment of the invention the sync-word 22 is used to set a time anchor point by the sensing hearing assistive device 31 to be used for synchronizing captured sensor signals returned to the requesting hearing assistive device 30. The data bits 23 are handled by the sensing hearing assistive device 31, and the data bits 23 may include instructions to start capturing synchronized or time-stamped physiologic sensor signals and send the captured physiologic sensor signals in one or more data packets 33 to the requesting hearing assistive device 30.

In one embodiment, the instructions in the synchronization message 32 specify the timing when the sensing hearing assistive device 31 must provide the response message containing the sensor data. By specifying to the sensing hearing devices 31 when to capture data and when to send data, the requesting hearing assistive device ensures that sensor data received by its processor from at least two sensors in wirelessly connected devices is synchronized before data processing in the requesting hearing assistive device 30.

Figure 4:
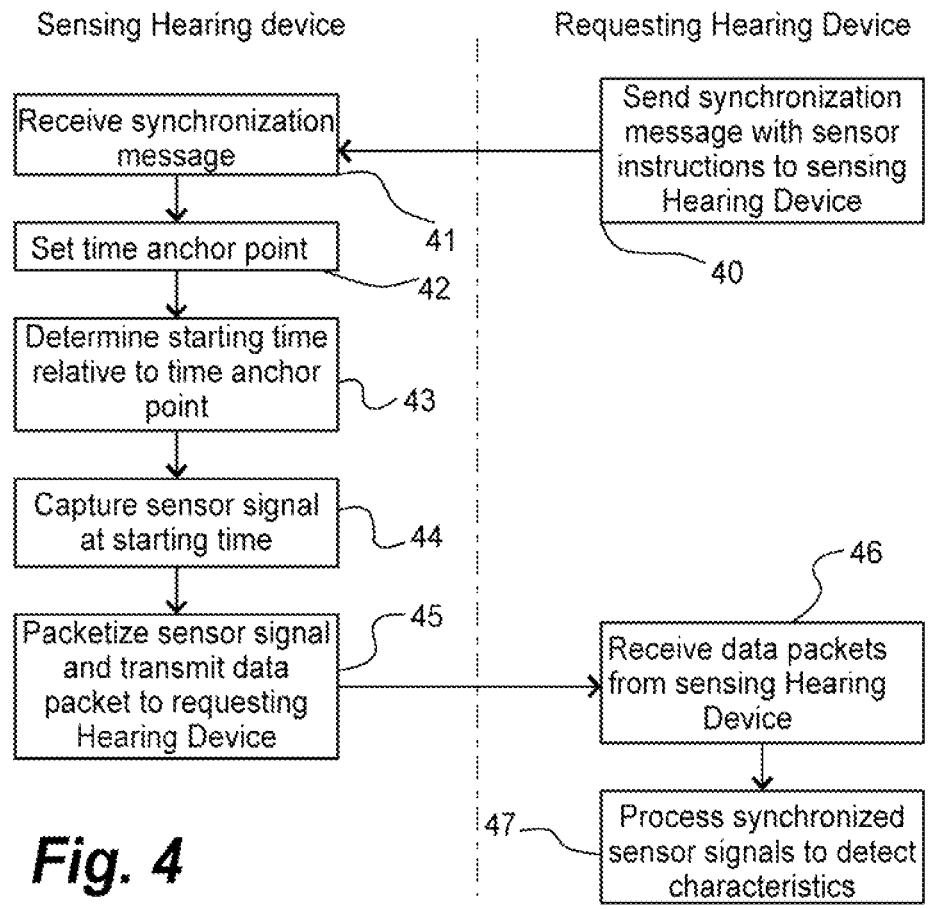
FIG. 4 shows a method for synchronizing sensor signal from a set of binaural hearing devices according to the invention.

FIG. 4 shows a flow chart illustrating a method for synchronizing sensor signal from wirelessly connected sensing devices according to the invention. In step 40 a requesting hearing assistive device 30 sends a synchronization message 32 with instructions to the sensing hearing devices 31. The sensing hearing assistive device 31 receives in step 41 the synchronization message 32, and in step 42 the sensing hearing assistive device 31 sets a time anchor point based upon the excellent auto correlation properties of the sync-word 22. In step 43, the sensing hearing assistive device 31, based on the instructions included in the synchronization message 32, determines the starting time set relatively to the time anchor point. According to the received instructions, the sensing hearing assistive device 31 starts in step 44 to capture a sensor signal at a predetermined point of time relatively to the time anchor point. In step 45 the sensing hearing assistive device 31 encodes the sensor signal into a digitized data packet and transmits this data packet to the requesting hearing assistive device 30. Normally the monitoring will require a continuous stream of digitized data packets transmitted to the requesting hearing assistive device 30.

The sensing hearing assistive device 31 will in the digitized data packets include timing metadata relevant for the signal processing in the requesting hearing assistive device 30. The requesting hearing assistive device 30 receives the continuous stream of digitized data packets from the sensing hearing device 31 in step 46. The requesting hearing assistive device 30 decodes the received data and timing metadata. In step 47, the sensor data received from the sensing hearing devices 31 is processed together with sensor data captured by the requesting hearing assistive device 30's own sensor to extract characteristics from the sensor data. The requesting hearing assistive device 30 ensures that the captured data is synchronized.

Normally the monitoring will require a continuous stream of digitized data packets transmitted to the requesting hearing assistive device 30. The sensing hearing assistive device 31 will in the digitized data packets include timing metadata relevant for the signal processing in the requesting hearing assistive device 30. The requesting hearing assistive device 30 receives the continuous stream of digitized data packets from the sensing hearing assistive device 31 in step 46. The requesting hearing assistive device 30 decodes the received data and timing metadata. In step 47, the sensor data collected from sensors distributed in the requesting hearing assistive device 30 and the sensing hearing assistive device 31 is processed in the requesting hearing assistive device 30 to extract characteristics from the sensor data. The requesting hearing assistive device 30 ensures that the captured data is synchronized.

In one embodiment, the sync-word 22 is constructed to ensure a large Hamming distance between sync-words 22 used in different communications supervised by the requesting hearing assistive device 30. This provides good auto correlation properties of the sync-word 22 which improves timing acquisition.

For capturing physiologic signals, the intended use of the signal specifies the required sample rate and sample size. In general, it is preferred to design sensors according to their intended purpose with predefined sample rate and sample size. The sensor may have to have a stimuli unit, if required, and a capturing unit.

Figure 5:
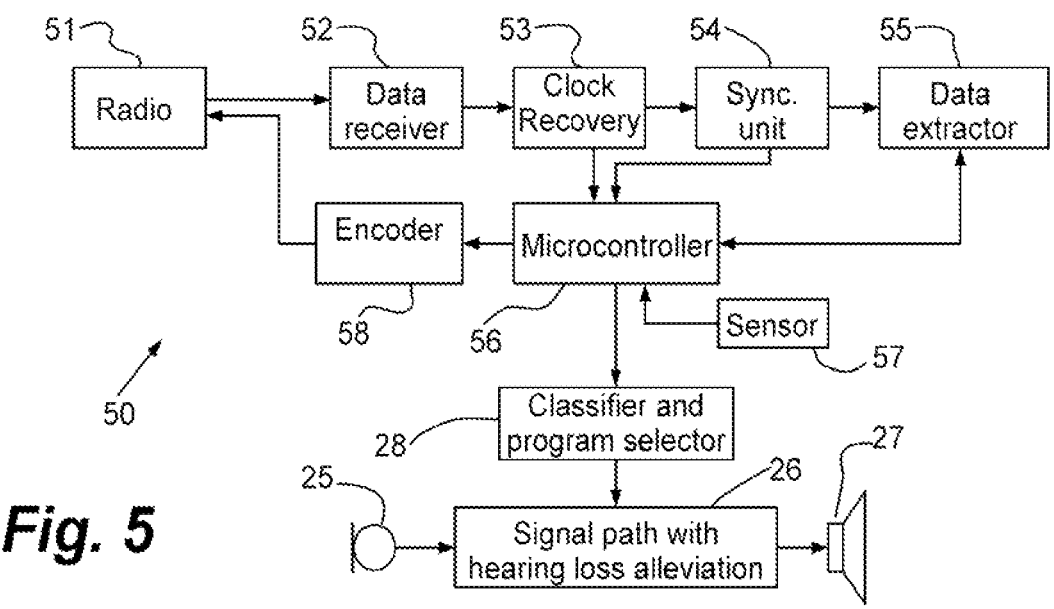
FIG. 5 illustrates the component of a hearing assistive device according to one embodiment of the invention.

FIG. 5 illustrates the components of a hearing assistive device 50 according to one embodiment of the invention. The hearing assistive device 50 has a transceiver or a radio 51 for communication with another hearing assistive device 50. The radio 51 may operate according to any suitable protocol, preferably a short-range radio protocol, as discussed above. A data receiver unit 52 receives the synchronization message 32 and isolates the payload 20 including the preamble 21, the sync-word 22 and data bits 23. A clock recovery unit 53 compares the system clock (not shown) of the sensing hearing assistive device 50 to the received preamble 21, and a microcontroller 56 adjusts the system clock accordingly. A synchronization unit 54 includes an auto correlator where the incoming data is correlated with the predetermined sync word 22. A data extraction unit 55 receives the data bits 23 and communicates the instructions to a microcontroller 56. By means of the input from the synchronization unit 54 and the data extraction unit 55, the microcontroller 56 determines the starting for sensor signal acquisition, and controls a sensor 57, e.g. an accelerometer, accordingly. The microcontroller 56 packetize the captured sensor signal and transmits data packets to the requesting hearing device by means of an encoder 58 and the radio 51.

The hearing assistive device 50 has at least one input transducer or microphones 25 picking up an audio signal. The audio signal is digitized and fed to digital signal processor 26 adapted for amplifying and conditioning of the audio signal intended to become presented for the hearing aid user. The amplification and conditioning are carried out according to a predetermined setting stored in in the hearing assistive device 50 to alleviate a hearing loss by amplifying sound at frequencies in those parts of the audible frequency range where the user suffers a hearing deficit. The amplification and conditioning audio signal is reproduced for the user via a speaker 27 or receiver. The microphone 25, digital signal processor 26, and speaker 27 provides an audio signal path with hearing loss alleviation. Furthermore, the hearing assistive device 50 includes a classifier and program selector component 28 analyzing the electric input signal from the microphone 25 and classifying an auditory environment of the hearing assistive device 50. The classifier and program selector component 28 automatically selects one of several modes of operation for digital signal processor 26 according to the classifier and program selector component 28's classification. These modes of operation may include beamforming of the microphones 25 or applying situation dependent noise reduction.

When the hearing assistive device 50 receives a sensor signal from a sensing hearing assistive device, the microcontroller 56 receives the wirelessly received sensor signal and the sensor signal from the sensor 57 and processes the synchronized sensor signal to detect and extract characteristics in the physiologic data. The extracted characteristics in the physiologic data is then used for program selection in the hearing assistive device 50. The program selection provided by the program selector component 28 operates in a multi-dimensional feature space based upon characteristics from the environment as well as characteristics derived from sensed physiologic parameters originating from the wearer of the hearing assistive device 50.

Figure 6:
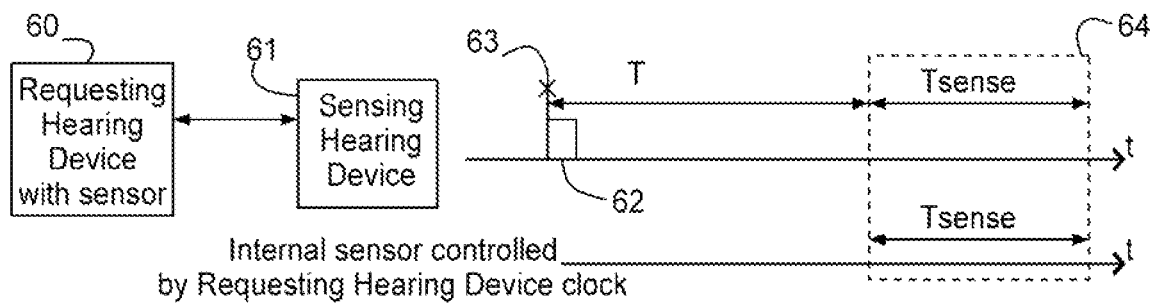
FIG. 6 illustrates an embodiment of a sensing hearing assistive device to be synchronized with the requesting hearing assistive device according to one embodiment of the invention.

FIG. 6 illustrates an embodiment with one sensor device in the sensing hearing assistive device 61 to be synchronized with the requesting hearing assistive device 61 according to one embodiment of the invention. The sensing hearing assistive device 61 is wirelessly connected to a requesting hearing assistive device 60. The requesting hearing assistive device 60 is responsible for the timing of the sensing hearing assistive device 61 having one or more sensors. The requesting hearing assistive device 60 include an accelerometer or other sensors.

The requesting hearing assistive device 60 sends a synchronization message 62 to the sensing hearing assistive device 61, and the sensing hearing assistive device 61 determines upon reception a time anchor point 63 as explained with reference to FIGS. 4 and 5. The sensing hearing devices 61 determines the duration, Tsense, of a sensing period 64, and the time, T, from the time anchor point 63 to the start of the sensing period 64. The requesting hearing assistive device 60 uses the time, T, and the duration, Tsense, of a sensing period 64 for activating its own sensor.

The sensing hearing assistive device 61 captures a sensor signal representing physiologic parameters and packetizes the captured sensor signals into payload of one or more data packets 33 (FIG. 3). In this embodiment, the sensing hearing assistive device 61 may have a unique ID. The unique ID is not necessarily necessary for the synchronization message 62 but may be valuable for signal encryption. Resynchronization of the sensor may be required from time to time.

Figure 7:
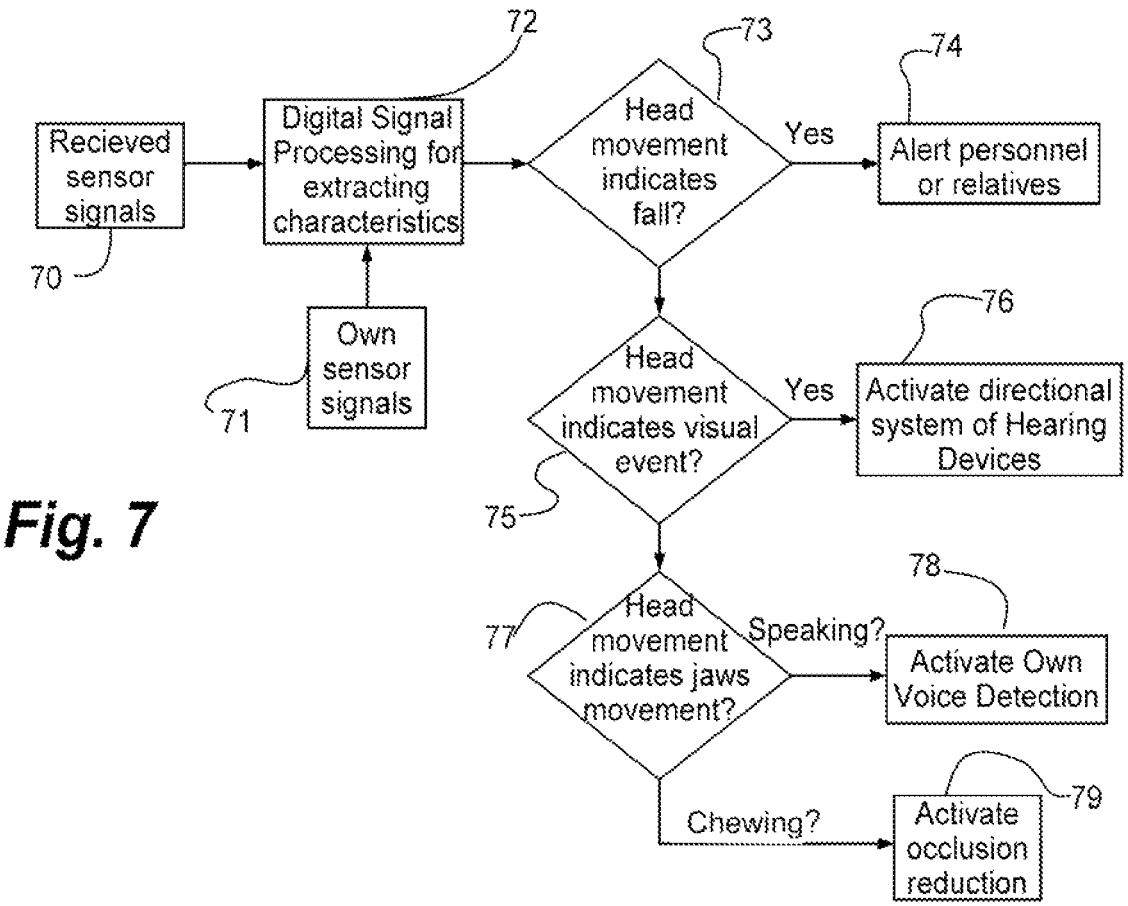
FIG. 7 illustrates a flowchart for acquiring sensor signal, processing the signal and controlling the hearing assistive device based on extracted characteristics.

Reference is made to FIG. 7 being a flowchart of a method carried out by the hearing assistive device 50 shown in FIG. 5. When an incoming sensor signal is received at step 70, the data extractor 55 prepares the sensor signal for processing by the microcontroller 56. The microcontroller 56 also receives sensor signals from its own sensor 56 at step 71. In this embodiment the sensor signals originate from accelerometers. By mean of its own timing scheme, the microcontroller 56 processes the at least two digital sensor signals at step 72 for extracting characteristics from the physiologic signals. In step 73, the processor 56 and the classifier and program selection component 28 classifies the extracted characteristics. If the extracted characteristics fulfils a first predetermined criterion, the extracted characteristics is determined to represent a fall. Then the personal communication device 10 may be used for alerting personnel or relatives in step 74.

In step 75, the extracted characteristics is compared to a second predetermined criterion, and if the extracted characteristics is determined to represent a fast turning of the head, this may indicate that the wearer of the hearing assistive devices reacts based upon a visual indication, e.g. has seen someone entering the room. Therefor the classifier and program selection component 28 activates the beam forming of the hearing assistive devices towards the direction the wearer looks in step 76.

In step 77, the extracted characteristics is compared to a third predetermined criterion in step 77 relating to jaws movement. If the jaws movement is likely to be speaking, then own voice detection may be activated to handle the effect of the reproduction of the wearer own voice in the hearing assistive devices in step 78, and if the jaws movement is likely to be caused by chewing, occlusion reduction may be activated in step 79.

The invention claimed is:

1. A hearing assistive system comprising a first hearing assistive device adapted for wireless communication with second hearing assistive device;
   wherein the first hearing assistive device and the second hearing assistive device each have at least one sensor adapted for acquiring a physiological signal;
   wherein the first hearing assistive device is adapted for
      providing a synchronization signal to the second hearing assistive device, and
      instructing the second hearing assistive device to acquire the physiological signal based on timing instructions,
   wherein the second hearing assistive device is adapted for
      acquiring the physiological signal by means of the sensor according to the received timing instructions,
      transmitting the acquired physiological signal wirelessly to the first hearing assistive device, and
   wherein the first hearing assistive device comprises a processor for processing the synchronized, physiological signals acquired by sensors of the first hearing assistive device and the second hearing assistive device and synchronized via wireless communication; and
   wherein the second hearing assistive device is adapted to
      receive a synchronization message,
      set a time anchor point based on the synchronization message, and
      acquire the physiological signal at a predetermined point of time relatively to the time anchor point.

2. The hearing assistive system according to claim 1, wherein the processor is adapted for extracting characteristics from the processed sensor signals, the extracted characteristics is used for controlling an audio signal path with hearing loss alleviation of the first hearing assistive device.

3. The hearing assistive system according to claim 1, wherein the time anchor point is set based on auto correlation of a sync-word included in the synchronization message.

4. The hearing assistive system according to claim 1, wherein the second hearing assistive device is adapted to encode the acquired physiological signal into a digitized data packet and transmit the data packet to the first hearing assistive device.

5. The hearing assistive system according to claim 4, wherein the second hearing assistive device is adapted to include timing metadata in the digitized data packet transmitted to the first hearing assistive device.

6. A hearing assistive system comprising a first hearing assistive device adapted for wireless communication with second hearing assistive device;
   wherein the first hearing assistive device and the second hearing assistive device each have at least one sensor adapted for acquiring a physiological signal;
   wherein the first hearing assistive device is adapted for
      providing a synchronization signal to the second hearing assistive device, and
      instructing the second hearing assistive device to acquire the physiological signal based on timing instructions,
   wherein the second hearing assistive device is adapted for
      acquiring the physiological signal by means of the sensor according to the received timing instructions,
      transmitting the acquired physiological signal wirelessly to the first hearing assistive device, and
   wherein the first hearing assistive device comprises a processor for processing the synchronized, physiological signals acquired by sensors of the first hearing assistive device and the second hearing assistive device and synchronized via wireless communication; and
   wherein the first hearing assistive device is adapted to
      receive digitized data packets from the second hearing assistive device,
      decode the received the digitized data packets to identify sensor data and timing metadata, and
      process the received sensor data in the processor to extract physiologic characteristics from the sensor data.

7. The hearing assistive system according to claim 1, wherein the processor is adapted for processing the synchronized, physiological signals acquired by a sensor present in the second hearing assistive device and a sensor present in the first hearing assistive device.

8. The hearing assistive system according to claim 1, wherein first hearing assistive device and the second hearing assistive device each include an accelerometer detecting a magnitude and direction of the acceleration of the hearing assistive device.

9. The hearing assistive system according to claim 1, wherein first hearing assistive device and the second hearing assistive device each include one electrode for sensing an EEG signal from the ear canal of the hearing assistive device user.

10. The hearing assistive system according to claim 1, wherein the processor is adapted for processing the synchronized, physiological signals acquired by sensors of at least two wirelessly connected hearing assistive devices in order to extract a physiological parameter.

11. A hearing assistive system comprising a first hearing assistive device adapted for wireless communication with second hearing assistive device;
   wherein the first hearing assistive device and the second hearing assistive device each have at least one sensor adapted for acquiring a physiological signal;
   wherein the first hearing assistive device is adapted for
      providing a synchronization signal to the second hearing assistive device, and
      instructing the second hearing assistive device to acquire the physiological signal based on timing instructions,
   wherein the second hearing assistive device is adapted for
      acquiring the physiological signal by means of the sensor according to the received timing instructions,
      transmitting the acquired physiological signal wirelessly to the first hearing assistive device, and
   wherein the first hearing assistive device comprises a processor for processing the synchronized, physiological signals acquired by sensors of the first hearing assistive device and the second hearing assistive device and synchronized via wireless communication;

wherein the processor is adapted for processing the synchronized, physiological signals acquired by sensors of at least two wirelessly connected hearing assistive devices in order to extract a physiological parameter;

wherein the hearing assistive device has at least two modes of operation; and wherein the processor is adapted to select one of the two modes of operation in dependence of the extracted physiological parameter.

12. A method of operating a hearing assistive system comprising a first hearing assistive device adapted for wireless communication with second hearing assistive device, the first hearing assistive device and the second hearing assistive device each have at least one sensor adapted for acquiring a physiological signal; wherein the method comprises steps of, providing, in the first hearing assistive device, a synchronization signal for the second hearing assistive device, instructing the second hearing assistive device to acquire the physiological signal based on timing instructions for synchronization, acquiring, in the second hearing assistive device, the physiological signal by means of the sensor according to the received timing instructions, transmitting the acquired physiological signal wirelessly to the first hearing assistive device, acquiring, in the first hearing assistive device, a physiological signal by means of the sensor according to the transmitted timing instructions, processing in the first hearing assistive device the synchronized, physiological signals acquired by the sensors in the first hearing assistive device and the second hearing assistive device; and wherein the second hearing assistive device is adapted to include timing metadata accompanied the acquired physiological signal transmitted to the first hearing assistive device.

13. The method according to claim 12, wherein the first hearing assistive device comprises a processor adapted for extracting characteristics from the processed sensor signals, the method comprises applying the extracted characteristics for controlling an audio signal path with hearing loss alleviation.

14. The hearing assistive system according to claim 6, wherein the processor is adapted for extracting characteristics from the processed sensor signals, the extracted characteristics is used for controlling an audio signal path with hearing loss alleviation of the first hearing assistive device.

15. The hearing assistive system according to claim 6, wherein the processor is adapted for processing the synchronized, physiological signals acquired by a sensor present in the second hearing assistive device and a sensor present in the first hearing assistive device.

16. The hearing assistive system according to claim 6, wherein first hearing assistive device and the second hearing assistive device each include an accelerometer detecting a magnitude and direction of the acceleration of the hearing assistive device.

17. The hearing assistive system according to claim 6, wherein first hearing assistive device and the second hearing assistive device each include one electrode for sensing an EEG signal from the ear canal of the hearing assistive device user.

18. The hearing assistive system according to claim 6, wherein the processor is adapted for processing the synchronized, physiological signals acquired by sensors of at least two wirelessly connected hearing assistive devices in order to extract a physiological parameter.

19. The hearing assistive system according to claim 11, wherein first hearing assistive device and the second hearing assistive device each include an accelerometer detecting a magnitude and direction of the acceleration of the hearing assistive device.

20. The hearing assistive system according to claim 11, wherein first hearing assistive device and the second hearing assistive device each include one electrode for sensing an EEG signal from the ear canal of the hearing assistive device user.

* * * * *